(12) United States Patent
Olsen

(10) Patent No.: US 8,756,983 B2
(45) Date of Patent: Jun. 24, 2014

(54) EROSION RESISTANT HARD COMPOSITE MATERIALS

(75) Inventor: Garrett T. Olsen, Conroe, TX (US)

(73) Assignee: Halliburton Energy Services, Inc., Houston, TX (US)

(*) Notice: Subject to any disclaimer, the term of this patent is extended or adjusted under 35 U.S.C. 154(b) by 458 days.

(21) Appl. No.: 12/902,511

(22) Filed: Oct. 12, 2010

(65) Prior Publication Data

US 2012/0017670 A1  Jan. 26, 2012

Related U.S. Application Data

(63) Continuation of application No. PCT/US2010/040065, filed on Jun. 25, 2010.

(51) Int. Cl.
*G01N 17/00* (2006.01)

(52) U.S. Cl.
USPC .................. 73/86; 73/7; 73/865.6

(58) Field of Classification Search
CPC ....... G01N 17/00; G01N 17/02; G01N 17/04; G01N 17/002; G01N 17/006; G01N 3/22; G01N 3/56
USPC ............... 73/7, 86, 865.6, 866, 760, 788, 847
See application file for complete search history.

(56) References Cited

U.S. PATENT DOCUMENTS

| | | | |
|---|---|---|---|
| 2,478,659 A * | 8/1949 | Jackson et al. ....................... 73/7 |
| 4,442,707 A * | 4/1984 | Tuzson ............................... 73/86 |
| 4,442,807 A * | 4/1984 | Latsch et al. ................... 123/263 |
| 4,493,206 A * | 1/1985 | Johnson et al. ....................... 73/7 |
| 4,814,234 A | 3/1989 | Bird |
| 4,872,345 A * | 10/1989 | Dicks .............................. 73/597 |
| 4,922,748 A * | 5/1990 | Hopenfeld ........................ 73/86 |
| 6,260,409 B1 * | 7/2001 | Briaud et al. ...................... 73/86 |
| 6,436,470 B1 | 8/2002 | Iacocca et al. |
| 6,469,278 B1 | 10/2002 | Boyce |
| 6,494,084 B1 * | 12/2002 | Roberts et al. .................... 73/86 |
| 6,659,206 B2 | 12/2003 | Liang et al. |
| 7,141,110 B2 | 11/2006 | Gray et al. |

(Continued)

FOREIGN PATENT DOCUMENTS

| | | |
|---|---|---|
| CA | 2672704 A1 | 7/2008 |
| WO | 2011162775 A1 | 12/2011 |

OTHER PUBLICATIONS

H.M. Hawthorne, Some Coriolis slurry erosion test developments, Tribology International, vol. 35, Issue 10, Oct. 2002, pp. 625-630.*

(Continued)

*Primary Examiner* — Hezron E Williams
*Assistant Examiner* — Hoang Nguyen
(74) *Attorney, Agent, or Firm* — McDermott Will & Emery LLP; Holly Soehnge

(57) ABSTRACT

A hard composite composition comprises a binder; and a polymodal blend of matrix powder. In an embodiment, the polymodal blend of matrix powder has at least one local maxima at a particle size of 30 μm or less, at least one local maxima at a particle size of 200 μm or more, and at least one local minima between a particle size of about 30 μm to about 200 μm that has a value that is less than the local maxima at a particle size of 30 μm or less.

19 Claims, 3 Drawing Sheets

(56) References Cited

U.S. PATENT DOCUMENTS

| | | | |
|---|---|---|---|
| 7,399,330 B2 | 7/2008 | Schwabel et al. | |
| 7,569,176 B2 | 8/2009 | Pope et al. | |
| 7,647,821 B2 * | 1/2010 | Bloomquist et al. | 73/86 |
| 8,100,203 B2 | 1/2012 | Lockwood et al. | |
| 8,261,632 B2 | 9/2012 | Stevens | |
| 2006/0074616 A1 | 4/2006 | Chen | |
| 2006/0288756 A1 * | 12/2006 | De Meurechy | 73/1.01 |
| 2007/0199379 A1 * | 8/2007 | Wolf et al. | 73/590 |
| 2008/0047894 A1 | 2/2008 | Trogolo et al. | |
| 2009/0110817 A1 | 4/2009 | Collin et al. | |
| 2009/0186211 A1 | 7/2009 | Chun et al. | |
| 2009/0283336 A1 | 11/2009 | Lockwood et al. | |
| 2010/0006345 A1 | 1/2010 | Stevens | |
| 2011/0088954 A1 | 4/2011 | DiGiovanni et al. | |
| 2011/0225896 A1 | 9/2011 | Vail | |
| 2011/0315051 A1 | 12/2011 | Olsen | |
| 2011/0315668 A1 | 12/2011 | Olsen | |
| 2013/0133951 A1 | 5/2013 | Olsen | |

OTHER PUBLICATIONS

Hawthorne et al., A new Coriolis slurry erosion tester design for improved slurry dynamics Original Research Article Wear, vol. 255, Issues 1-6, Aug.-Sep. 2003, pp. 170-180.*

Search Report and Written Opinion for International Patent Application No. PCT/US10/040065 dated Aug. 19, 2010.

Search Report for EP Patent Application No. EP 2 607 511 dated Oct. 3, 2013.

* cited by examiner

EROSION RESISTANT HARD COMPOSITE MATERIALS

This application is a continuation of copending U.S. Patent Application Serial No. PCT/US10/040,065 entitled "Erosion Resistant Hard Composite Materials," filed on Jun. 25, 2010, the entirety of which is herein incorporated by reference.

BACKGROUND

The present invention relates to a matrix powder composition for use along with a binder to form a hard composite material. More particularly, the invention pertains to a matrix powder composition for use along with a binder to form a hard composite material wherein the hard composite material exhibits improved erosion resistance while retaining strength. The matrix powder compositions of the present invention may be useful for tools that are involved in any application or operation in which a tool may be subjected to erosive and/or abrasive conditions. Examples include subterranean applications that involve the use of drill bits for drilling a well bore.

Hard composite materials have been formed by incorporating one or more particulate elements within a matrix powder, and then infiltrating the matrix powder with a binder metal to form a composite material with the particulate elements incorporated within. This composite material can be useful in tools or other devices that are subject to erosion. Composite materials may include diamond composites material that can comprise a suitable binder with one or more discrete diamond-based particulate elements held therein. Additional particulate elements that have been used include tungsten carbide. Tungsten carbide can be used in various forms including, but not limited to, macrocrystalline tungsten carbide and cast tungsten carbide.

Hard composite materials have been used for a variety of purposes, including the manufacturing of earth-boring drill bits to provide some erosion resistance and improve mechanical strength. For example, polycrystalline diamond compact ("PDC") cutters are known in the art for use in earth-boring drill bits. Typically, drill bits using PDC cutters include an integral bit body, which may substantially incorporate a hard composite. A plurality of PDC cutters can be mounted along the exterior face of the bit body in extensions of the bit body called "blades." Each PDC cutter has a portion which typically is brazed in a recess or pocket formed in the blade on the exterior face of the bit body. The PDC cutters are positioned along the leading edges of the bit body blades so that as the bit body is rotated, the PDC cutters engage and drill the earth formation. In use, high forces may be exerted on the PDC cutters, particularly in the forward-to-rear direction. Additionally, the bit and the PDC cutters may be subjected to substantial abrasive and erosive forces.

While steel body bits may have toughness and ductility properties that make them resistant to cracking and failure due to impact forces generated during drilling, steel is more susceptible to erosive wear caused by high-velocity drilling fluids and formation fluids that carry abrasive particles, such as sand, rock cuttings, and the like. Generally, steel body bits often may be coated with a more erosion-resistant material, such as tungsten carbide, to improve their erosion resistance. However, tungsten carbide and other erosion-resistant materials are relatively brittle relative to steel. During use, a thin coating of the erosion-resistant material may crack, peel-off or wear, exposing the softer steel body which is then rapidly eroded. This can lead to loss of cutters as the area around the cutter is eroded away, causing the bit to fail.

Hardfacing is another example where hard composite materials have been used. Hardfacing of metal surfaces and substrates is a technique to minimize or prevent erosion and abrasion of the metal surface or substrate. Hardfacing can be generally defined as applying a layer or layers of hard, abrasion resistant material to a less resistant surface or substrate by plating, welding, spraying or other well known deposition techniques. Hardfacing is frequently used to extend the service life of drill bits and other downhole tools. Tungsten carbide and its various forms are some of the more widely used hardfacing materials to protect drill bits and other downhole tools associated with drilling and producing oil and gas wells.

Rotary cone drill bits are often used for drilling boreholes for the exploration and production of oil and gas. This type of bit typically employs three rolling cone cutters, also known as rotary cone cutters, rotatably mounted on spindles extending from support arms of the bit. The cutters are mounted on respective spindles that typically extend downwardly and inwardly with respect to the bit axis so that the conical sides of the cutters tend to roll on the bottom of a borehole and contact the formation. For some applications, milled teeth are formed on the cutters to cut and gouge in those areas that engage the bottom and peripheral wall of the borehole during the drilling operation. The service life of milled teeth may be improved by the addition of tungsten carbide particles to hard metal deposits on selected wear areas of the milled teeth by hardfacing.

Current composite materials can suffer from mass or material loss when subject to an abrasive and/or erosive environment. This mass or material loss can lead to tool failure or limited service life of the tool, possibly resulting in non-productive time (NPT). NPT is undesirable. Reducing NPT through extended service life of the tool would be advantageous. As such, it would be desirable to provide an improved hard composite material having improved properties that include impact strength, transverse rupture strength, hardness, abrasion resistance, and erosion resistance.

SUMMARY

The present invention relates to a matrix powder composition for use along with a binder to form a hard composite material. More particularly, the invention pertains to a matrix powder composition for use along with a binder to form a hard composite material wherein the hard composite material exhibits improved erosion resistance while retaining strength.

An embodiment of the invention comprises a hard composite composition comprising a binder; and a polymodal blend of matrix powder. En an embodiment, the polymodal blend of matrix powder has at least one local maxima at a particle size of 30 μm or less, at least one local maxima at a particle size of 200 μm or more, and at least one local minima between a particle size of about 30 μm to about 200 μm that has a value that is less than the local maxima at a particle size of 30 μm or less.

Another embodiment of the invention comprises a drill bit comprising: a bit body; and at least one cutting element for engaging a formation; wherein at least a portion of the bit body comprises a hard composite material comprising: a binder; a polymodal blend of matrix powder, wherein the polymodal blend of matrix powder has a local maxima at a particle size of 30 μm or less, a local maxima at a particle size of 200 μm or more, and a local minima between a particle size of about 30 μm to about 200 μm that has a value that is less than the local maxima at a particle size of 30 μm or less.

Still another embodiment of the invention comprises a method comprising: providing a drill bit comprising: a bit body comprising: a binder; a polymodal blend of matrix powder wherein the polymodal blend of matrix powder has a local maxima at a particle size of 30 μm or less, a local maxima at a particle size of 200 μm or more, and a local minima between a particle size of about 30 μm to about 200 μm that has a value that is less than the local maxima at a particle size of 30 μm or less; and at least one cutting element for engaging a formation; and drilling a well bore in a subterranean formation with the drill bit.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

DESCRIPTION OF THE PREFERRED EMBODIMENTS

Figure 1:
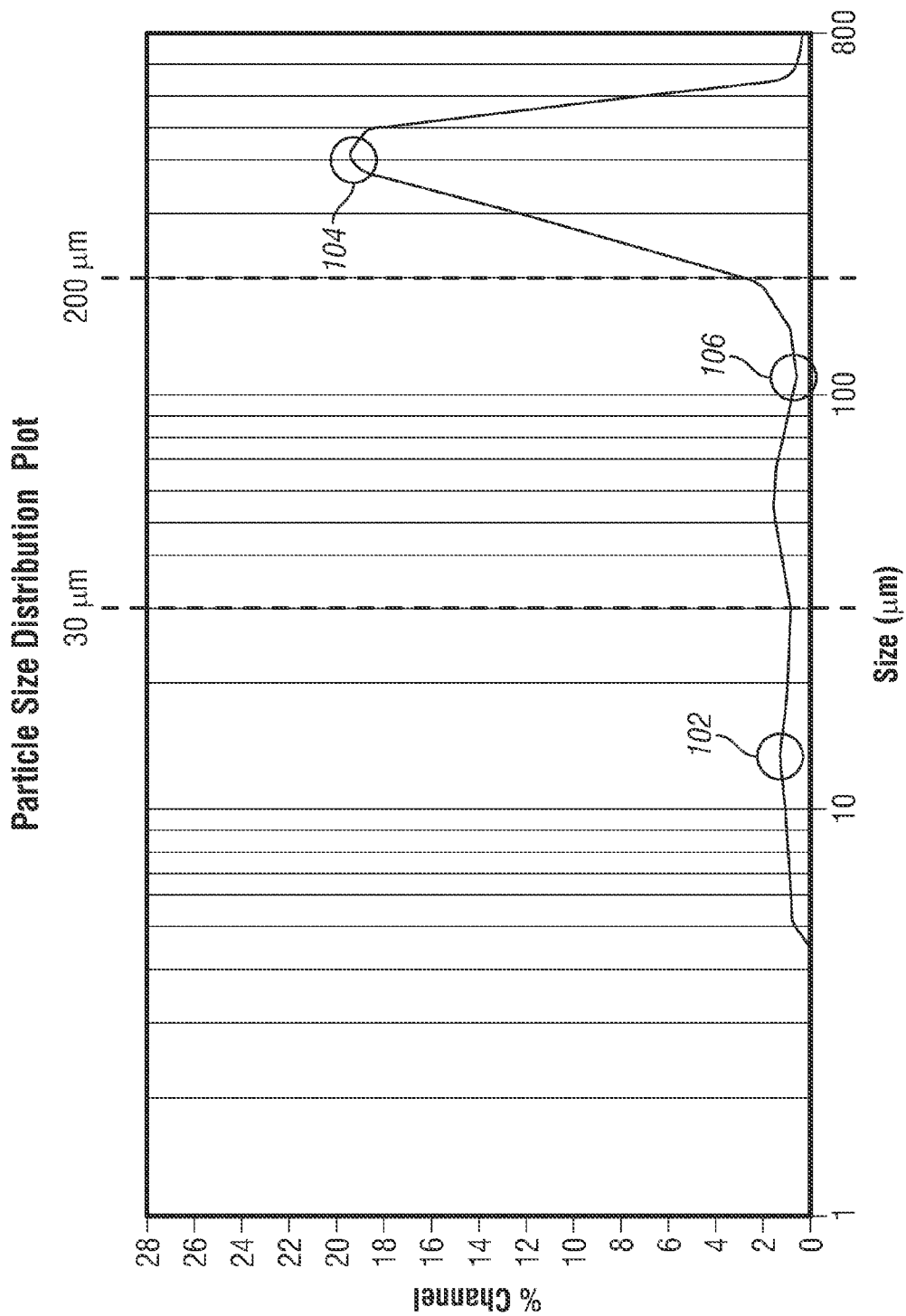
FIG. 1 is a particle size distribution plot showing a particle size distribution for an embodiment of a polymodal blend of matrix powder.

The present invention relates to a matrix powder composition for use along with a binder to form a hard composite material. More particularly, the invention pertains to a matrix powder composition for use along with a binder to form a hard composite material wherein the hard composite material exhibits improved erosion resistance while retaining strength. The matrix powder compositions of the present invention may be useful for tools that are involved in any application or operation in which a tool may be subjected to erosive and/or abrasive conditions. Examples include subterranean applications that involve the use of drill bits for drilling a well bore.

While many advantages of the present invention exist, only a few are discussed herein. Without intending to be limited by theory, for hard composite materials, there is generally a tradeoff between improving the erosion resistance of a material and improving and/or maintaining its mechanical strength. In general, additives added to the composite materials to improve the erosion resistance tend to cause the material to become brittle with a corresponding decrease in the mechanical strength. Conversely, additives used to improve the mechanical strength tend to reduce the erosion resistance of the material. Striking the appropriate balance can be difficult.

The hard composite materials of the present invention provide both erosion resistance and mechanical strength at desirable levels. For example, in an embodiment of the present invention, a hard composite material comprising a polymodal blend of matrix powder and a binder may improve the erosion resistance of the material while improving and/or maintaining its mechanical strength at desirable levels. As used herein, "maintaining mechanical strength" may depend on the particular application of the composite material and the specifications attendant thereto. Generally, it refers to the composite material being in line with the minimum required mechanical strength specifications. The polymodal blend of matrix powder enables the realization of both erosion resistance and mechanical strength due, at least in pail, to the polymodal particle size distribution. Thus, the resulting hard composite material may be able to better withstand abrasion, wear, erosion and other stresses associated with repeated use in a abrasive and/or erosive environment.

Also disclosed are components produced using the hard composite materials. For example, drill bits and hardfacing materials comprising the hard composite materials can be used to improve the erosion resistance of various components used in a subterranean environment. In some embodiments, a drill bit may be formed from a hard composite material according to the present invention or a layer of hardfacing prepared from a hard composite material may be deposited on selected exterior surfaces of a drill bit. Both of these applications may extend the service life of the drill bit during downhole drilling.

In an embodiment, a hard composite material composition according to the present invention comprises a binder, and a polymodal blend of matrix powder. The polymodal aspects of the blend described herein are relative to a final blend of the matrix powder.

The following is understood in the context of a particle size distribution plot (e.g., particle size v.s. vol % channel) such as those available from the "S3500 Particle Size Analyzer" available from MicroTrac Inc. (2008) in Montgomeryville, Pa. using standard testing protocols recommended by the manufacturer in the 2008 manual for the equipment using the default channel widths. FIG. 1 is an example of such a plot.

As used herein, a "polymodal" blend of matrix powder refers to matrix powder with two or more different modes. As used herein, "modes" refers to a local maxima on a particle size distribution plot. In an embodiment, the polymodal blend of matrix powder has at least one local maxima at a particle size of 30 μm or less (alternatively 20 μm or less, 10 μm or less, or 5 μm or less) as measured in an "S3500 Particle Size Analyzer" available from MicroTrac Inc. (2008) in Montgomeryville, Pa. using standard testing protocols recommended by the manufacturer in the 2008 manual for the equipment. The term "local maxima" as used herein refers to a value at which the slope of the curve is about zero where the line transitions from a positive slope to a negative slope in the direction of increasing particle size. The polymodal blend of matrix powder has at least one local maxima at a particle size of 200 μm or more (alternatively 250 μm or more, 300 μm or more, or 400 μm or more) as measured in an S3500 Dry Powder Measuring Machine available from MictroTrac. The polymodal blend of matrix powder also has at least one local minima between a particle size of about 30 μm (alternatively 20 μm or less, 10 μm or less, or 5 μm or less) to about 200 μm (alternatively 250 μm or more, 300 μm or more, or 400 μm or more) that has a value that is less than the local maxima at a particle size of 30 μM or less (alternatively 20 μm or less, 10 purr or less, or 5 μm or less). The term "local minima" as used herein refers to a value at which the slope of the curve is about zero where the line transitions from a negative slope to a positive slope in the direction of increasing particle size. The local maxima and local minima can be one or more points on a plot that has zero slope; if a single point, the slope may be considered undefined by some, but for purposes of this disclosure, that single point is considered to have a zero slope.

FIG. 1 illustrates a particle size distribution of an example of a hard composite material composition of the present invention comprising a polymodal blend of matrix powder. FIG. 1 is an example of a plot from an S3500 Particle Size Analyzer available from MictroTrac, which is used to describe the polymodal blend of matrix powder and compositions of the present invention. Shown at 102 is an example of a first local maxima. Shown at 104 is an example of a second local maxima. Comparatively shown at 106 is an example of a local minima that is less than local maxima 102.

The polymodal blend of matrix powder useful with the present invention generally lends erosion resistance to the hard composite material along with a high resistance to abrasion, erosion and wear. The polymodal blend of matrix powder can comprise particles of any erosion resistant materials which can be bonded (e.g., mechanically) with a binder to form a hard composite material. Suitable materials may include, but are not limited to, carbides, nitrides, natural and/or synthetic diamonds, and any combination thereof.

In an embodiment, a matrix powder may comprise tungsten carbide (WC). Various types of tungsten carbide may be used with the present invention, including, but not limited to, stoichiometric tungsten carbide particles, cemented tungsten carbide particles, and/or cast tungsten carbide particles. The first type of tungsten carbide, stoichiometric tungsten carbide, may include macrocrystalline tungsten carbide and/or carburized tungsten carbide. Macrocrystalline tungsten carbide is essentially stoichiometric WC in the form of single crystals, but some multicrystals of WC may form in larger particles. In some embodiments, macrocrystalline tungsten carbide may comprise additions of cast carbide, Ni, Fe, Carbonyl of Fe, Ni, etc. Macrocrystalline tungsten carbide may also have characteristics such as hardness, wettability and response to contaminated hot, liquid binders which are different from cemented carbides or spherical carbides. Methods of manufacturing macrocrystalline tungsten carbide are known to those of ordinary skill in the art.

Carburized tungsten carbide, as known in the art, is a product of the solid-state diffusion of carbon into tungsten metal at high temperatures in a protective atmosphere. Carburized tungsten carbide grains are typically multi-crystalline (e.g., they are composed of WC agglomerates). The agglomerates may form grains that are larger than individual WC crystals. Typical carburized tungsten carbide may contain a minimum of 99.8% by weight of carbon infiltrated WC, with a total carbon content in the range of about 6.08% to about 6.18% by weight.

The second type of tungsten carbide, cemented tungsten carbide, may include sintered spherical tungsten carbide and/or crushed cemented tungsten carbide. The terms "cemented carbide" and "cemented carbides" may be used within this application to include WC, MoC, TiC, TaC, NbC, $Cr_3C_2$, VC and solid solutions of mixed carbides such as WC—TiC, WC—TiC—TaC, WC—TIC—(Ta,Nb)C in a particulate binder (matrix) phase. The binder materials used to form cemented carbides may sometimes be referred to as "bonding materials" in this patent application to help distinguish between binder materials used to form cemented carbides and binder materials used to form a hard composite material and tools incorporating the hard composite materials. Cemented carbides may sometimes be referred to as "composite" carbides or sintered carbides. Sintered tungsten carbide is commercially available in two basic forms: crushed and spherical (or pelletized). Crushed sintered tungsten carbide is produced by crushing sintered components into finer particles, resulting in more irregular and angular shapes, whereas pelletized sintered tungsten carbide is generally rounded or spherical in shape. The particulate bonding material provides ductility and toughness which often results in greater resistance to fracture (toughness) of cemented carbide pellets, spheres or other configurations as compared to cast carbides, macrocrystalline tungsten carbide and/or formulates thereof.

A typical process for making cemented tungsten carbide generally includes providing a tungsten carbide powder having a predetermined size (or within a selected size range), and mixing the powder with a suitable quantity of cobalt, nickel, or other suitable bonding material. The mixture is typically prepared for sintering by either of two techniques: it may be pressed into solid bodies often referred to as green compacts, or alternatively, the mixture may be formed into granules or pellets such as by pressing through a screen, or tumbling and then screened to obtain more or less uniform pellet size. Such green compacts or pellets are then heated in a controlled atmosphere furnace to a temperature near the melting point of cobalt (or the like) to cause the tungsten carbide particles to be bonded together by the metallic phase. Sintering globules of tungsten carbide specifically yields spherical sintered tungsten carbide. Crushed cemented tungsten carbide may further be formed from the compact bodies or by crushing sintered pellets or by forming irregular shaped solid bodies. The particle size, morphology, and quality of the sintered tungsten carbide can be tailored by varying the initial particle size of tungsten carbide and cobalt, controlling the pellet size, adjusting the sintering time and temperature, and/or repeated crushing larger cemented carbides into smaller pieces until a desired size is obtained.

The third type of tungsten carbide, cast tungsten carbide, may include spherical cast tungsten carbide and/or crushed cast tungsten carbide. Cast tungsten carbide has approximately the eutectic composition between bitungsten carbide, $W_2C$, and monotungsten carbide, WC. Cast carbide is typically made by heating tungsten in contact with carbon. Processes for producing spherical cast carbide particles are known to those of ordinary skill in the art. For example, tungsten may be heated in a graphite crucible having a hole through which a resultant eutectic mixture of $W_2C$ and WC may drip. This liquid may be quenched in a bath of oil and may be subsequently crushed to a desired particle size to form what is referred to as crushed cast tungsten carbide. Alternatively, a mixture of tungsten and carbon is heated above its melting point into a constantly flowing stream which is poured onto a rotating cooling surface, typically a water-cooled casting cone, pipe, or concave turntable. The molten stream is rapidly cooled on the rotating surface and forms spherical particles of eutectic tungsten carbide, which are referred to as spherical cast tungsten carbide.

Additional materials useful as matrix powder or as part of a matrix powder blend include, but are not limited to, silicon nitride ($Si_3N_4$), silicon carbide (SiC), boron carbide ($B_4C$) and cubic boron nitride (CBN). For purposes of the present application, the term cubic boron nitride refers to an internal crystal structure of boron atoms and nitrogen atoms in which the equivalent lattice points are at the corner of each cell. Boron nitride particles typically have a diameter of approximately one micron and appear as a white powder. Boron nitride, when initially formed, has a generally graphite-like, hexagonal plate structure. When compressed at high pressures (such as $10^6$ PSI) cubic boron nitride particles will be formed with a hardness very similar to diamonds. However, the mechanical strength of cubic boron nitride is generally low in comparison with many steel alloys.

The various materials useful as a matrix powder may be selected so as to provide a polymodal blend of matrix powder and final hard composite material that is tailored for a particular application. For example, the type, shape, and/or size of a particulate material used in the formation of a hard composite material may affect the material properties of the material, including, for example, fracture toughness, transverse rupture strength, and erosion resistance. In an embodiment, the polymodal blend of matrix powder can comprise a single material or a blend of materials. In addition, two or more matrix powders may be combined as necessary to form the polymodal blend of matrix powder with the characteristics described herein.

Without intending to be limited by theory, it is believed that the matrix powder with the larger particle size distribution may be at least partly responsible for the improved erosion resistance of a hard composite material formed using the polymodal blend of matrix powder. Similarly, the matrix powder with the smaller particle size distribution may be at least partly responsible for maintaining the mechanical properties (e.g., fracture toughness, transverse rupture strength, etc.) of a hard composite material formed from the polymodal blend of matrix powder.

The terms "binder" or "binder material" may be used in this application to include copper, cobalt, nickel, iron, zinc, manganese, any alloys of these elements, any combinations thereof, or any other material satisfactory for use in forming a hard composite material comprising the polymodal blend of matrix powder described above. Such binders generally provide desired ductility, toughness and thermal conductivity for an associated hard composite material. Binder materials may cooperate with the particulate material(s) present in the matrix powders selected in accordance with teachings of the present disclosure to form hard composite materials with increased erosion resistance as compared to many conventional hard composite materials.

The hard composite materials of the present invention may be formed using any technique known in the art. A typical formation process for casting hard composite materials may begin by forming a mold in the shape of a desired component. Displacement materials such as, but not limited to, mold inserts, and additives necessary to obtain the desired shape may then be loaded into the mold assembly. The mold assembly may then be loaded with the polymodal blend of matrix powder. As the mold assembly is being tilled, a series of vibration cycles may be used to assist packing of the polymodal blend of matrix powder, as necessary. The vibrations may help ensure a consistent density of the matrix powders within a desired range required to achieve the desired characteristics for the hard composite material.

The binder material may then be placed on top of the mold assembly, and may be optionally covered with a flux layer. A cover or lid may be placed over the mold assembly as necessary. The mold assembly and materials disposed therein may be preheated and then placed in a furnace. When the furnace temperature reaches the melting point of the binder material, the resulting liquid binder material may infiltrate the polymodal blend of matrix powder. The mold assembly may then be cooled below the solidus temperature to form the hard composite material. The mold assembly may be removed to allow the hard composite material that is the shape of a desired component to be removed for use. Use of this procedure may allow for a variety of components to be formed from the hard composite materials described herein.

In an embodiment, a hard composite material of the present invention may display improved erosion resistance while maintaining or improving its mechanical strength. The improved erosion resistance may be measured by an improvement in the volume loss (e.g., an improvement represents a reduction in the volume loss and/or erosion rate) of a sample when subjected to a Slurry Erosion Test procedure (a "SET" procedure), which has been developed to test the hard composite materials produced according to the present invention. While not intending to be limited by theory, it is believed that the SET procedure allows a measurement of the erosion resistance of a material under conditions that more closely match those encountered in a subterranean formation during drilling or any other treatment operation involving erosive conditions than other test procedures currently available.

The SET procedure can be used to determine the erosion rate for a sample of a material. First, a test specimen can be provided and the mass and density of the test specimen may be measured and recorded. A testing container may be provided that is suitably sized to hold the test specimen along with an erosion material. In an embodiment, a plastic container with a volume from about 50 mL, to about 2 L can be used as the test container for small samples, though a larger container constructed of an appropriate material can be used for larger samples. The erosion material can be any suitable abrasive material capable of eroding the test specimen. In an embodiment, fine silica powder may be used as the erosion material. The erosion material is placed in the testing container, water may be added, and the container may be agitated to thoroughly mix the erosion material and the water. In an embodiment, a sufficient amount of water may be added to form a slurry and may typically comprise about 20% to about 99% of the volume of the testing container. The ratio of erosion material to water may be varied to model a specific density fluid, as desired (e.g., a drilling mud). One of ordinary skill in the art can determine the ratio of erosion material to water based on the desired density of fluid. The test specimen may be placed in the testing container and the testing container may be sealed. The testing container may be loaded into a device capable of moving the sample through the slurry within the testing container. For example, a 3-dimensional blender/mixer as known to one of ordinary skill in the art may be used. The mixer may be started and the beginning time may be recorded. The testing container may be then agitated for a period of time. The time period selected may depend on the test specimen size, the erosion material, and the test specimen composition. In an embodiment, the time period may range from about 1 to about 72 hours. In general, the test results may be scalable based on time. The mixer may then be stopped and the time recorded. The test specimen can be removed, rinsed, and dried prior to measuring and recording the mass and density of the test specimen. The mass loss can be calculated as the difference between the initial mass and the final mass. The volume loss can be calculated based on the mass loss and the initial and final densities. A volume loss percentage can be calculated based on the volume loss and the initial volume. An erosion rate can then be determined on a mass or volume basis by dividing the mass loss or volume loss, respectively, by the test run time.

The test specimen can then be retested according to the same procedure outlined above at least two more times. In a preferred embodiment, fresh erosion material and water may be used for each test. Reusing the erosion material may result in skewed results due, at least in part, to the wearing of the erosion material during the previous testing procedures. But the erosion material may be reused in successive tests, if desired, as long as that variable is taken into account when evaluating the results. Due to the geometric variations in the test samples, the first run in the test procedure may show a higher volume loss percentage than subsequent runs. The second and third runs may be averaged, along with any additional runs, to determine the erosion rate and volume loss percentage for the test specimen.

In an embodiment, a "specific SET procedure" may be used to determine the erosion rate on either a mass or volume basis according to the following parameters. First, a test specimen of material with a mass of between about 1 g and 50 g is provided and the mass and density of the test specimen is measured and recorded. A 500 mL plastic test container is provided, and a 100 g fine silica powder sample is used as the erosion material. The silica powder is placed in the testing container, 375 g of water is added, and the container is agitated to thoroughly mix the erosion material and the water. The test specimen is placed in the testing container and the testing container is sealed. The testing container is loaded into a 3-dimensional blender/mixer (e.g., a "Turbula Shaker Mixer Type T2 F" available from Willy A. Bachofen AG Mashinenfabrik of Switzerland, or equivalent) and set to a mixing speed of 34 $min^{-1}$, where the effective speed of the mixer depends on several influences, and may not exactly correspond to the set speed. The mixer is started and the beginning time is recorded. The testing container is then agitated for a period of about 24 hours. The mixer is stopped and the time recorded. The test specimen is removed, rinsed, and dried prior to measuring and recording the mass and density of the test specimen. The mass loss can be calculated as the difference between the initial mass and the final mass. The volume loss can be calculated based on the mass loss and the initial and final densities. A volume loss percentage can be calculated based on the volume loss and the initial volume. The test procedure is then repeated at least 2 additional times using fresh silica powder and water for each run. The average values of the mass loss and volume loss from the second and subsequent runs is then used to determine erosion rate on a mass or volume basis by dividing the mass loss or volume loss, respectively, by the test run time.

In an embodiment, a hard composite material produced according to the present invention may have an erosion rate of less than 0.06% vol/hr as determined by the specific SET procedure outlined above. In another embodiment, a hard composite material produced according to the present invention may have an erosion rate of less than 0.055% vol/hr, or alternatively less than 0.053% vol/hr as determined by the specific SET procedure outlined above.

In an embodiment, the hard composite materials of the present invention may be used to form at least a portion of a rotary drill bit. Rotary drill bits can be used to drill oil and gas wells, geothermal wells and water wells. Rotary drill bits may be generally classified as rotary cone or roller cone drill bits and fixed cutter drilling equipment or drag bits. Fixed cutter drill bits or drag bits are often formed with a matrix bit body having cutting elements or inserts disposed at select locations of exterior portions of the matrix bit body. Fluid flow passageways are typically formed in the matrix bit body to allow communication of drilling fluids from associated surface drilling equipment through a drill string or drill pipe attached to the matrix bit body. Such fixed cutter drill bits or drag bits may sometimes be referred to as "matrix drill bits." The terms "matrix drill bit" and "matrix drill bits" may be used in this application to refer to "rotary drag bits," "drag bits," "fixed cutter drill bits."

Figure 2:
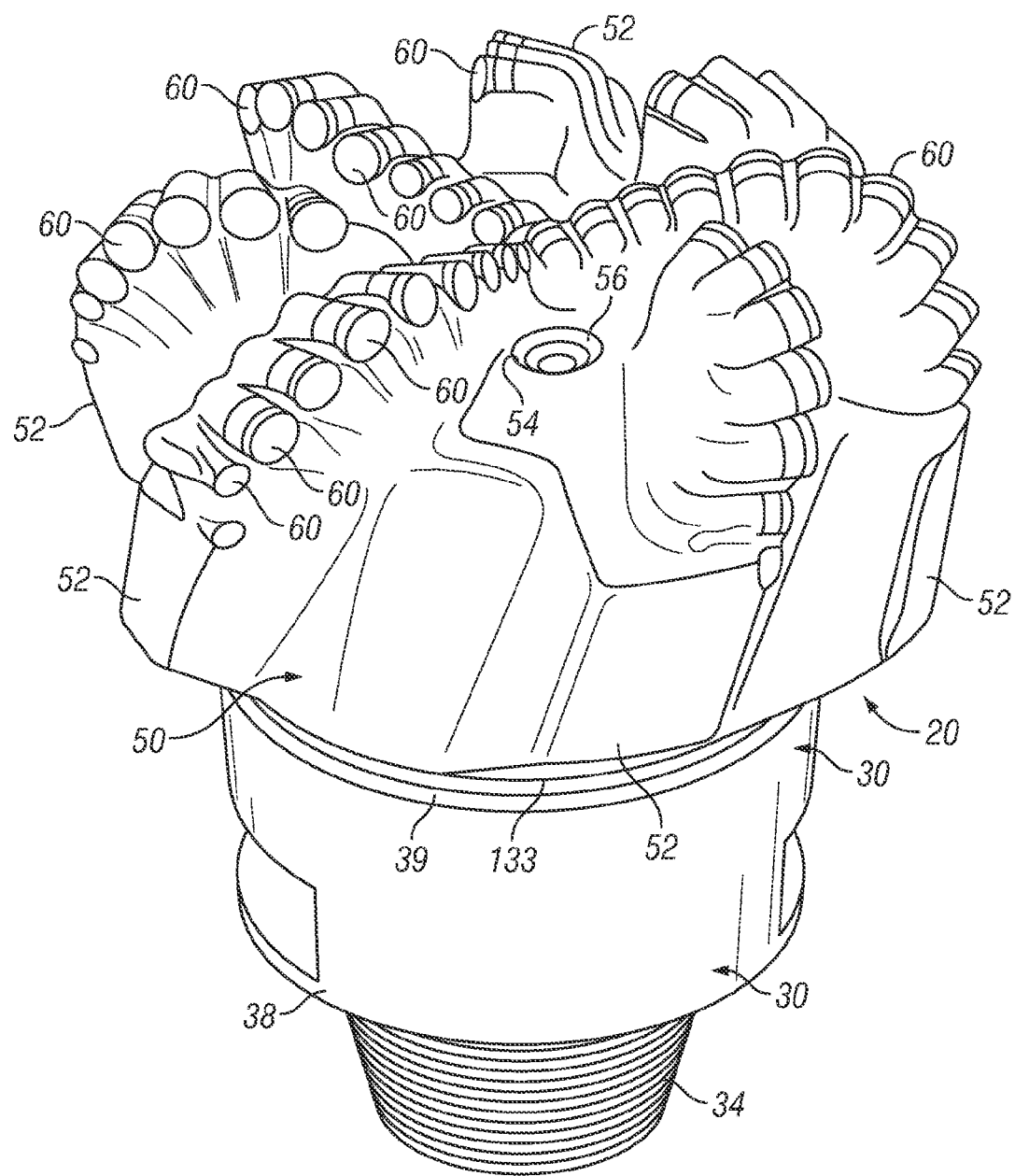
FIG. 2 is a schematic drawing showing an isometric view of an embodiment of a fixed cutter drill bit having a hard composite material bit body formed in accordance with the teachings of the present disclosure.

FIG. 2 is a schematic drawing showing one example of a matrix drill bit or fixed cutter drill bit that may be formed with a hard composite material in accordance with teachings of the present disclosure. For embodiments such as shown in FIG. 2, matrix drill bit 20 may include metal shank 30 with hard composite material bit body 50 securely attached thereto. Metal shank 30 may be described as having a generally hollow, cylindrical configuration defined in part by a fluid flow passageway therethrough. Various types of threaded connections, such as American Petroleum Institute (API) connection or threaded pin 34, may be formed on metal shank 30 opposite from hard composite material bit body 50.

In some embodiments, a generally cylindrical metal blank or casting blank may be attached to hollow, generally cylindrical metal shank 30 using various techniques. For example annular weld groove 38 may be formed between adjacent portions of the blank and shank 30. Weld 39 may be formed in grove 38 between the blank and shank 30. The fluid flow passageway or longitudinal bore preferably extends through metal shank 30 and the metal blank. The metal blank and metal shank 30 may be formed from various steel alloys or any other metal alloy associated with manufacturing rotary drill bits.

A matrix drill bit may include a plurality of cutting elements, inserts, cutter pockets, cutter blades, cutting structures, junk slots, and/or fluid flow paths that may be formed on or attached to exterior portions of an associated bit body. For an embodiment such as shown in FIGS. 2, a plurality of cutter blades 52 may form on the exterior of hard composite material bit body 50. Cutter blades 52 may be spaced from each other on the exterior of hard composite material bit body 50 to form fluid flow paths or junk slots therebetween.

A plurality of nozzle openings 54 may be formed in hard composite material bit body 50. Respective nozzles 56 may be disposed in each nozzle opening 54. For some applications nozzles 56 may be described as "interchangeable" nozzles. Various types of drilling fluid may be pumped from surface drilling equipment (not expressly shown) through a drill string (not expressly shown) attached with threaded connection 34 and the fluid flow passageways to exit from one or more nozzles 56. The cuttings, downhole debris, formation fluids and/or drilling fluid may return to the well surface through an annulus (not expressly shown) formed between exterior portions of the drill string and interior of an associated well bore (not expressly shown).

A plurality of pockets or recesses may be formed in blades 52 at selected locations. Respective cutting elements or inserts 60 may be securely mounted in each pocket to engage and remove adjacent portions of a downhole formation. Cutting elements 60 may scrape and gouge formation materials from the bottom and sides of a well bore during rotation of matrix drill bit 20 by an attached drill string. In some embodiments, various types of polycrystalline diamond compact (PDC) cutters may be satisfactorily used as inserts 60. A matrix drill bit having such PDC cutters may sometimes be referred to as a "PDC bit".

U.S. Pat. No. 6,296,069 entitled Bladed Drill Bit with Centrally Distributed Diamond Cutters and U.S. Pat. No. 6,302,224 entitled Drag-Bit Drilling with Multiaxial Tooth Inserts, both incorporated herein in their entirety, show various examples of blades and/or cutting elements which may be used with a composite matrix bit body incorporating teachings of the present disclosure. It will be readily apparent to persons having ordinary skill in the art that a wide variety of fixed cutter drill bits, drag bits and other drill bits may be satisfactorily formed with a hard composite material bit body incorporating teachings of the present disclosure. The present disclosure is not limited to hard composite material drill bit 20 or any specific features as shown in FIG. 2.

Matrix drill bits can be formed according to the present invention by placing a polymodal blend of matrix powder into a mold and infiltrating the hard composite material with a binder. The mold may be formed by milling a block of material such as graphite to define a mold cavity with features that correspond generally with desired exterior features of the resulting matrix drill bit. Various features of the resulting matrix drill bit such as blades, cutter pockets, and/or fluid flow passageways may be provided by shaping the mold cavity and/or by positioning temporary displacement material within interior portions of the mold cavity. A preformed steel shank or bit blank may be placed within the mold cavity to provide reinforcement for the matrix bit body and to allow attachment of the resulting matrix drill bit with a drill string. Once the quantity of the polymodal blend of matrix powder is placed within the mold cavity, the mold may be infiltrated with a molten binder which can form a hard composite material bit body after solidification of the binder with the polymodal blend of matrix powder.

A matrix drill bit may be formed using the hard composite materials of the present invention that may have a functional gradient. In this embodiment, one or more portions of the matrix drill bit (e.g., an outer layer) may be formed using the polymodal blend of matrix powder disclosed herein, while a different material composition is used to form the remaining portions of the matrix drill bit (e.g., the interior portions). As an example, a resulting matrix drill bit can be described as having a "functional gradient" since the outer portions may have improved erosion resistance while the inner portions may exhibit improved mechanical strength by having a different material composition. Methods of forming matrix drill bits with different functional zones is described in U.S. Pat. No. 7,398,840 entitled Matrix Drill Bits and Method of Manufacturing, which is incorporated herein in its entirety.

A tool comprising a hard composite material in whole or in part as formed in accordance with the teachings of the present invention may be used for other applications in a wide variety of industries and is not limited to downhole tools for the oil and gas industry.

Figure 3:
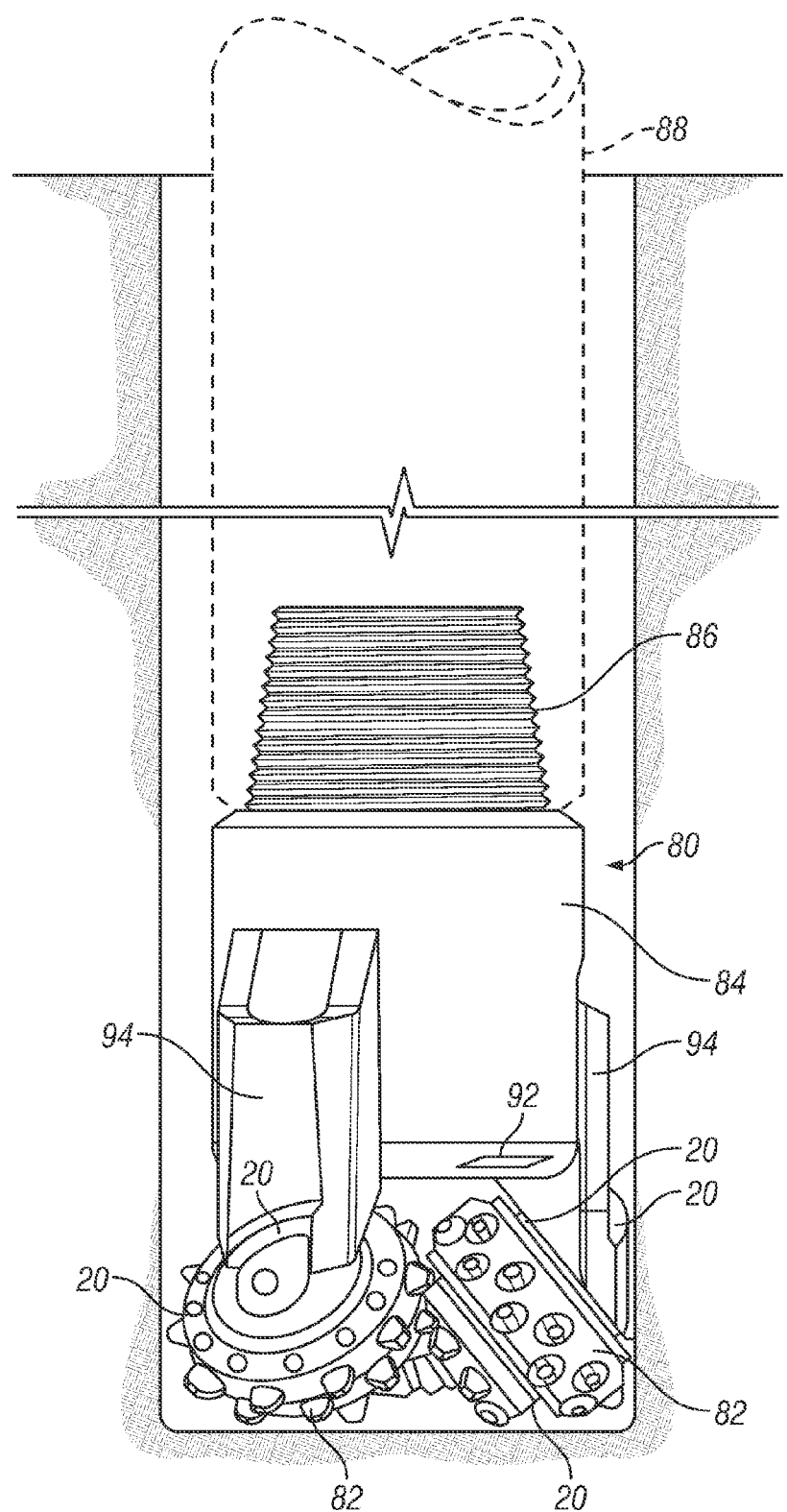
FIG. 3 is a schematic drawing in section elevation showing an embodiment of a drill bit formed in accordance with the teachings of the present invention at a downhole location in a well bore.

In an embodiment, the hard composite materials of the present invention may be used to form at least a portion of a rotary cone drill bit. FIG. 3 is a schematic drawing showing one example of a rotary cone drill bit that may be formed with a hard composite material in accordance with teachings of the present disclosure. For embodiments such as shown in FIG. 3, drill bit 80 includes a bit body 84 adapted to be connected at its pin or threaded connection 86 to the lower end of rotary drill string 88. Threaded connection 86 and the corresponding threaded connection of the drill string are designed to allow rotation of drill bit 80 in response to rotation of the drill string 88 at the well surface (not shown). Bit body 84 includes a passage (not shown) that provides downward communication for drilling mud or the like passing downwardly through the drill string. The drilling mud exits through nozzle 92 and is directed to the bottom of the borehole and then passes upward in the annulus between the wall of the borehole and the drill string, carrying cuttings and drilling debris therewith. Depending from bit body 84 are three substantially identical arms 94. Only two arms 94 are shown in FIG. 3. The lower end portion of each of the arms 94 is provided with a bearing pin or spindle (not shown), to rotatably support generally conical cutter cone assembly 82. On each cutter cone assembly 82 are milled teeth capable of eroding the formation face when placed in contact with the formation.

The cutting action or drilling action of a rotary cone drill bit occurs as the cutter cone assemblies are rolled around the bottom of the borehole by the rotation of an associated drill string. The cutter cone assemblies may be referred to as "rotary cone cutters" or "roller cone cutters." The inside diameter of the resulting borehole is generally established by the combined outside diameter, or gage diameter, of the cutter cone assemblies. The cutter cone assemblies may be retained on a spindle by a conventional ball retaining system comprising a plurality of ball bearings aligned in a ball race.

Rotary cone drill bits can be manufactured from a strong, ductile steel alloy, selected to have good strength, toughness and reasonable machinability. Such steel alloys generally do not provide good, long term cutting surfaces and cutting faces on the respective cutter cone assemblies because such steel alloys are often rapidly worn away during downhole drilling operations. To increase the downhole service life of the respective rotary cone drill bits, a hard composite material as disclosed herein may be used to form at least a portion of the shirttail surfaces, the backface surfaces, the milled teeth, and/or the inserts associated with the rotary cone drill bits. Hard composite material may also be used to form any other portions of the rotary cone drill bits that are subjected to intense erosion, wear and abrasion during downhole drilling operations. For some applications, essentially all of the portions of the rotary cone drill bits with exposed, exterior surfaces may be formed using a hard composite material of the present invention. For example, spindle surfaces 20 may be formed using a hard composite material according to the present invention.

In an embodiment, a desired component can be hardfaced using a hard composite material of the present invention to improve the wear and erosion resistance of the component. Hardfacing can be defined as applying a layer or layers of hard, abrasion resistant material comprising a hard composite material as disclosed herein to a less resistant surface or substrate by plating, welding, spraying or other well known deposition techniques. Hardfacing can be used to extend the service life of drill bits and other downhole tools used in the oil and gas industry.

A hard composite material may be formed on and/or bonded to working surface of a substrate using various techniques associated with hardfacing. In some embodiments, the hard composite material may be applied by welding techniques associated with conventional hardfacing. In an embodiment, the hard composite materials may be applied by welding by first forming a welding rod or similar structure comprising the hard composite material and/or a hard composite material precursor (i.e., a mixture of the polymodal blend of matrix powder and a binder, which may be in particulate form). In an embodiment, a welding rod may include a hollow tube which is closed at both ends to contain a hard composite material comprising a polymodal blend of matrix powder, and optionally, a binder in particulate form. In some embodiments, the hollow tube may comprise the binder material that, once melted, forms the hard composite material with the polymodal blend of matrix powder contained therein. Alternatively, the welding rod may comprise a solid rod of the hard composite material, and may optionally comprise additional additives as described in more detail below. En an embodiment, the hard composite material may be included as part of a continuous welding rod, composite welding rod, or welding rope.

In some embodiments, the welding rod may optionally comprise a deoxidizer and a temporary resin binder. Examples of deoxidizers satisfactory for use with the present invention include various alloys of iron, manganese, and silicon. The welding rod may comprise additional, optional materials such as powders of hard material selected from the group consisting of tungsten, niobium, vanadium, molybdenum, silicon, titanium, tantalum, zirconium, chromium, yttrium, boron, carbon and carbides, nitrides, or oxides. The welding rod may also optionally include a powdered mixture selected from the group consisting of copper, nickel, iron, cobalt and alloys of these elements to act as a binder when hardfacing a substrate. The specific compounds and elements selected for inclusion in the welding rod may depend upon the intended application for the resulting hard composite material the substrate, and the selected welding technique.

During the welding process, the surface of a substrate may be sufficiently heated to melt portions of the substrate and form metallurgical bonds between the hard composite material and the substrate. In addition to oxyacetylene welding, atomic hydrogen welding techniques, tungsten inert gas (TIG-GTA), stick welding or SMAW and GMAW welding techniques may be satisfactorily used to apply the hard composite material to a surface of a substrate.

In some embodiments, the hard composite material may be formed directly on the surface of a substrate. In these embodiments, a mixture of the polymodal blend of matrix powder and the binder in particulate form may be blended with an organic resin and sprayed on a surface of a substrate. A laser may then be used to densify and fuse the resulting powdered mixture with the surface of the substrate to form the desired metallurgical bonds as previously discussed. Tube rod welding with an oxyacetylene torch may be satisfactorily used to form metallurgical bonds between hard composite material and substrate and metallurgical bonds between matrix portion and coating. For other applications, laser welding techniques may be used to form hard composite material on substrate. Both tube rod welding techniques and laser welding techniques are known to those of ordinary skill in the art.

For some less stringent applications, hard composite material may be formed on a substrate using plasma spray techniques and/or flame spray techniques, which are both associated with various types of hardfacing. Plasma spray techniques typically form a mechanical bond between the resulting hard composite material in the hardfacing and the associated substrate. Flame spraying techniques also typically form a mechanical bond between the hard composite material in the hardfacing and the substrate. For some applications, a combination of flame spraying and plasma spraying techniques may also be used to form a metallurgical bond between the hard composite material and the substrate. In general, hardfacing techniques which produce a metallurgical bond are preferred over those hardfacing techniques which provide only a mechanical bond between the hard composite material and the substrate.

In an embodiment, forming a hardfacing comprising a hard composite material formed in accordance with the teachings of the present invention may be used on a wide variety of metallic bodies and substrates. For example, a hardfacing comprising a hard composite material may be placed on roller cone drill bits, fixed cutter drill bits, sleeve for drill bits, coring bits, underreamers, hole openers, stabilizers and shock absorber assemblies. A hardfacing comprising a hard composite material formed in accordance with the teachings of the present invention may be used on other tools in a wide variety of industries and is not limited to downhole tools for the oil and gas industry.

Any suitable hardfacing techniques or methods can be used with the hard composite materials of the present invention. Additional suitable hardfacing techniques that can incorporate the hard composite material of the present invention are described in U.S. Pat. No. 6,469,278 entitled Hardfacing Having Coated Ceramic Particles or Coated Particles of Other Hard Materials, which is incorporated herein in its entirety.

To determine if a device has incorporated a hard composite material of the present invention having a polymodal blend of matrix powder, certain imaging techniques may be suitable. An example of a suitable analysis technique is available from Smart Imaging Technologies in Houston, Tex. The software involved as of the time of this invention is "SIMAGIS®." Metallographic images of the infiltrated hard composite material may be uploaded into the SIMAGIS software. Contrasting techniques known in the art may be used, if needed. Metallographic images are analyzed by the software to determine particle size distribution for components of the hard composite material that has been incorporated into the device. The SIMAGIS presentation of data may vary from the data from the Microtrac particle size analyzer due to, among other things, channel width which may differ between the two techniques. The data from both techniques may be correlated by one skilled in the art.

In an embodiment, a method comprises providing a drill bit comprising a bit body formed from a hard composite material. The hard composite material generally comprises a binder, and a polymodal blend of matrix powder. In some embodiments, the polymodal blend of matrix powder has a local maxima at a particle size of 30 µm or less, a local maxima at a particle size of 200 µm or more, and a local minima between a particle size of about 30 µm to about 200 µm that has a value that is less than the local maxima at a particle size of 30 µm or less. The drill bit also has at least one cutting element for engaging a formation. The drill bit is then used to drill a well bore in a subterranean formation.

To facilitate a better understanding of the present invention, the following examples of certain aspects of some embodiments are given. In no way should the following examples be read to limit, or define, the scope of the invention.

EXAMPLES

A series of experiments, were carried out according to the specific SET procedure described above. First, a test specimen of material with a mass of between about 2 g and 30 g was provided and the mass and density of the test specimen was measured and recorded. The formulations of each specimen are shown below in Table 1. Test samples 1 through 4 were formulated as provided by the manufacturer. Test samples 5 and 6 were prepared according to the methods disclosed herein.

TABLE 1

| Sample No. | Composition |
| --- | --- |
| 1 | D63, available from Halliburton Energy Services of Houston, TX |
| 2 | D63, available from Halliburton Energy Services of Houston, TX |
| 3 | P90, available from Kennametal Inc. of Latrobe, PA |
| 4 | P90, available from Kennametal Inc. of Latrobe, PA |
| 5 | Polymodal blend of matrix powder Sample 1 |
| 6 | Polymodal blend of matrix powder Sample 2 |

The samples were testing using a 500 mL plastic test container, and 100 g of fine silica powder sample. The silica powder was placed in the testing container, 375 g of water was added, and the container was agitated to thoroughly mix the erosion material and the water. The test specimen was placed in the testing container and the testing container was sealed. The testing container was loaded into a 3-dimensional blender/mixer. The mixer was started and the beginning time was recorded. The testing container was then agitated for a period of time. The mixer was stopped and the time recorded. The test specimen was removed, rinsed, and dried prior to measuring and recording the mass and density of the test specimen. The mass loss was calculated as the difference between the initial mass and the final mass. The volume loss was calculated based on the mass loss and the initial and final densities. A volume loss percentage was calculated based on the volume loss and the initial volume. The test procedure was then repeated 3 additional times using fresh silica powder and water for each run. The values of the volume loss were then used to determine erosion rate on a volume basis by dividing the volume loss by the test run time. The results for each sample are presented below in Table 2.

TABLE 2

| | Test Run Volume Loss Per Hour (% of initial volume) | | | | |
|---|---|---|---|---|---|
| Sample | 1 | 2 | 3 | 4 | Average of runs 2-4 (% vol. loss/hr) |
| 1 | 0.063% | 0.065% | 0.061% | 0.063% | 0.063% |
| 2 | 0.063% | 0.065% | 0.061% | 0.063% | 0.063% |
| 3 | 0.095% | 0.094% | 0.086% | 0.088% | 0.089% |
| 4 | 0.095% | 0.094% | 0.086% | 0.088% | 0.089% |
| 5 | 0.061% | 0.057% | 0.052% | 0.053% | 0.054% |
| 6 | 0.058% | 0.056% | 0.052% | 0.052% | 0.053% |

The results demonstrate to one of ordinary skill in the art that the formulations according to the present invention reduce the erosion rate as measured by the volume loss per time relative to comparative samples. Test samples 5 and 6 as prepared according to the teachings of the present disclosure show an erosion rate below those of the other comparative samples.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method of testing a sample for erosion comprising:
   providing a test specimen;
   measuring a first mass and a first density of the test specimen;
   placing the test specimen in a testing container with a slurry that comprises an erosion material and a fluid;
   freely moving the test specimen through the slurry in the test container for a period of time;
   removing the test specimen from the testing container;
   measuring and recording at least one of a second mass and a second density of the test specimen; and
   calculating an erosion rate for the test specimen.

2. The method of claim 1 wherein the erosion material comprises fine silica powder.

3. The method of claim 1 wherein the fluid comprises water.

4. The method of claim 1 wherein the slurry is modeled after a drilling mud.

5. The method of claim 1 wherein the testing container is a 3-dimensional blender/mixer.

6. The method of claim 1 wherein the period of time ranges from about 1 hour to about 72 hours.

7. The method of claim 1 further comprising calculating a volume loss percentage based on the volume loss and the initial volume.

8. The method of claim 1 further comprising calculating a mass loss percentage based on the difference between the initial mass and the final mass.

9. The method of claim 1 wherein calculating the erosion rate is done by dividing the mass loss by the test run time.

10. The method of claim 1 wherein calculating the erosion rate is done by dividing the volume loss by the test run time.

11. The method of claim 1 wherein the test method is repeated more than one time on a single test specimen.

12. A method of testing a sample for erosion comprising:
    providing a test specimen of material with a mass of between about 1 g and 50 g;
    measuring the mass and density of the test specimen;
    placing the test specimen in a test container with a slurry, the slurry comprising a fluid and an erosion material;
    placing the testing container in a 3-dimensional blender/mixer;
    mixing the testing container for a time period greater than 1 hour such that the test specimen freely moves through the slurry in the test container;
    removing the test specimen from the test container;
    measuring the mass and density of the test specimen; and
    calculating an erosion rate for the test specimen.

13. The method of claim 12 wherein the erosion material comprises fine silica powder.

14. The method of claim 12 wherein the fluid comprises water.

15. The method of claim 12 wherein the slurry is modeled after a drilling mud.

16. The method of claim 12 wherein the period of time ranges from about 1 hour to about 72 hours.

17. The method of claim 12 further comprising calculating a volume loss percentage based on the volume loss and the initial volume.

18. The method of claim 12 further comprising calculating a mass loss percentage based on the difference between the initial mass and the final mass.

19. The method of claim 12 wherein calculating the erosion rate is done by dividing the mass loss by the test run time.

* * * * *